United States Patent

Lukić

Patent Number: 5,843,939
Date of Patent: *Dec. 1, 1998

[54] DERIVATIVES OF 3-BROMO- AND 3,3-DIBROMO-4-OXO-1-AZETIDINES, PROCESSES FOR THE PREPARATION THEREOF AND THEIR USE

[75] Inventor: Irena Lukić, Zagreb, Croatia

[73] Assignee: PLIVA, farmaceutska, kemijska, prehrambena i kozmeticka industrija, dionicko drustvo, Zagreb, Croatia

[*] Notice: The term of this patent shall not extend beyond the expiration date of Pat. No. 5,670,638.

[21] Appl. No.: 796,708

[22] Filed: Feb. 6, 1997

[30] Foreign Application Priority Data

Feb. 6, 1996 [HR] Croatia ................... P960061A
Jan. 20, 1997 [HR] Croatia ................... P970036A

[51] Int. Cl.$^6$ ................. A61K 31/395; C07D 205/08
[52] U.S. Cl. ................. 514/210; 540/354; 540/360; 540/361
[58] Field of Search ................. 540/354, 360, 540/361; 514/210

[56] References Cited

U.S. PATENT DOCUMENTS

| | | | |
|---|---|---|---|
| 4,140,593 | 2/1979 | Mitzlaff | 540/360 |
| 4,427,586 | 1/1984 | Numata | 540/361 |
| 4,595,539 | 6/1986 | Hamanaka | 540/360 |

OTHER PUBLICATIONS

Martel, Can J Chem 61, 1899 1983.
Sanoza, Zetraheehan 44, 7007 (1988).
Lattrella, Chem, Abs 74, 12982n (1974).

*Primary Examiner*—Mark L. Berch
*Attorney, Agent, or Firm*—Pollock, Vande Sande & Priddy

[57] ABSTRACT

3-Bromo- and 3,3-dibromo-4-oxo-1-azetidines of the formula I

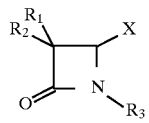

wherein $R_1$ is hydrogen or bromo, $R_2$ is hydrogen or bromo, $R_3$ is hydrogen,

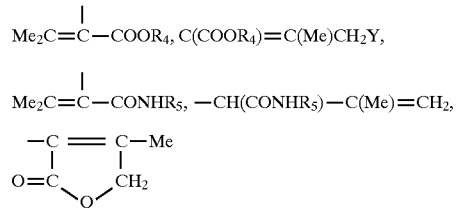

wherein $R_4$ is hydrogen, methyl, benzyl or some other protective group, $R_5$ is hydrogen, alkyl, alkylaryl, a heterocyclic ring, Y is a halo atom, X is a halo atom, alkoxy group, nitroxy group are provided along with processes for the preparation thereof and the use thereof. The 3-bromo- and 3,3-dibromo-4-oxo-1-azetidines can be prepared by reacting 2-sulfinic acid derivatives, with various halogenating agents, and after treating the reaction mixture, 2-halo derivatives of 3-bromo- and 2,2-dibromo-4-oxo-azetidines are isolated and are subjected to a reaction with silver tetrafluoroborate and alcohols to give the corresponding 2-alkoxy derivatives of 3-bromo- and 3,3-dibromo-4-oxo azetidines, or 2-halo derivatives of 3-bromo- and 3-3-dibromo-4-oxo azetidines are subjected to a reaction with silver nitrate in 2-propanol to give, after treating the reaction mixture, 2-nitroxy derivatives of 3-bromo and 3,3-dibromo-4-oxo-1-azetidines. Some newly prepared compounds are deprotected and derivatives having a free carboxy group are obtained. The prepared compounds are components in pharmaceutical compositions effective in antibacterial or antirumour therapy.

14 Claims, No Drawings

DERIVATIVES OF 3-BROMO- AND 3,3-DIBROMO-4-OXO-1-AZETIDINES, PROCESSES FOR THE PREPARATION THEREOF AND THEIR USE

TECHNICAL FIELD

The invention relates to derivatives of 3-bromo- and 3,3-dibromo-4-oxo-1-azetidines, to processes for the preparation thereof and to the use thereof.

Certain 2-chloro derivatives of 3-phthalimido-alpha-(1-methylethylidene)-4-oxo-1-azetidine acetic acid are well-known and are prepared by a reaction of methyl 6-phthalimido penicillanate with chlorine or sulfuryl chloride (S. Kukolja, J. Am. Chem. Soc. 93, (1971), 6267).

2-haloazetidinones are also prepared by a reaction of penicillin with halogenating agents such as molecular chlorine or N-halosuccinimide (U.S. Pat. No. 4,159,984). Further there is disclosed a rearrangement of oxoazetidine sulfinic acids obtained from penicilline sulfoxide with halogenating agents into 2-haloazetidinones (W. A. Spitzer, S. Kukolja, T. Goodson. J. P. Lammert, R. Steven, Eli Lilly Co., EP appln. 0060120 of 15 Sep. 1982, U.S. application Ser. No. 241,872 of 9 Mar. 1981; and W. A. Spitzer, T. Goodson, S. R. Lammert, S. Kukoija; J. Org. Chem. 46, (1981) 3569). Narisada et al. described a synthesis of 2-chloroazetidinone from methylthioazetidinones obtained from penicillins (U.S. Pat. No. 4,138,486).

S. Kukolja and S. R. Lammert further described the preparation of the above 2-chloro derivatives, but this time starting from a trichloroethyl ester of 6-phenyl-acetamido-penicillanate (Croat. Chem. Acta 44 (1972) 299–301). Eli Lilly patented the preparation of 2-haloazetidinones starting from 3-exomethylene cephalosporine sulfones with an acylamide group in the 7-position by the reaction thereof with activated zinc or magnesium and ammonium chloride to obtain sulfinic acids, which with halogenating agents gave sulfinyl chlorides, which were then subjected to hydrolysis (EP 0132395 A).

3-bromo- and 3,3-dibromo-2-chloroazetidinones were also prepared by the reaction of pivaloyloxymethyl 6-bromo- or 6,6-dibromopenicillinates with chlorine or tert.-butyl hypochlorite (C. Somoza and O. A. Oreste, Tetrahedron 44, (1988) 7007–12). In the same article the authors disclosed 2-tert.-butoxy derivatives of 3-bromo- and 3,3-dibromo-azetidinones.

Methyl esters of 2-chloro-alpha-(1-bromomethylethylidene)-4-oxo-1-azetidine acetic acid with phthalimido trichloroethoxycarbonylamino or phenoxycarbonylamino group in C-3 position were described by Saul Wolfe et al. (Can. J. Chem. 50, (1972) 2898 and Can. J. Chem. 60. (1982) 144).

According to the Applicant's EP 0633247 A1 2-bromo- and 2-nitroxy derivatives of 3-bromo- and 3,3-dibromo-4-oxo-azetidines may be prepared by the reaction of 1,1-dioxide derivatives of protected penicillanic acids with the treatment with DBN reagent and thionyl chloride and by passing the obtained product through a silica gel column or by treatment with tetrabutyl ammonium bromide wherein derivatives of 2-bromo-, 3-bromo- or 2-bromo-3,3-dibromo-4-oxoazetidines are isolated, which may be subsequently subjected to the reaction with silver nitrate in 2-propanol and after the treatment of the reaction mixture derivatives of 2-nitroxy-3-bromo- or 2-bromo-3,3-dibromo-4-oxoazetidines are isolated.

According to our knowledge of the Prior Art, certain derivatives of 3-bromo- and 3,3-dibromo-4-oxo-azetidines are not known.

The object of the present invention are derivatives of 3-bromo- and 3,3-dibromo-4-oxo-1-azetidines of the general formula I

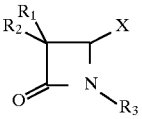

wherein
$R_1$ is hydrogen or bromo,
$R_2$ is hydrogen or bromo,
$R_3$ is hydrogen,

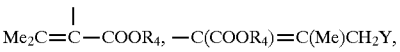

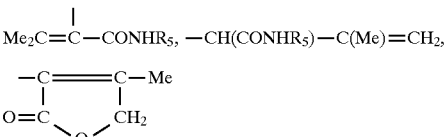

wherein
$R_4$ is hydrogen, methyl, benzyl or some other protective group,
$R_5$ is hydrogen, alkyl, alkylaryl, a heterocyclic ring,
Y is a halo atom,
X is a halo atom, alkoxy group, nitroxy group.

Another object of the present invention is a process for the preparation of derivatives of 3-bromo- and 3,3-dibromo-4-oxo-1-azetidines of the general formula I, wherein the radicals have the above meanings, and the said derivatives may be prepared starting from sulfinic acid derivatives of the general formula II

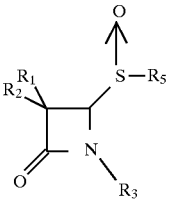

wherein
$R_1$ is hydrogen or bromo,
$R_2$ is hydrogen or bromo,
$R_3$ is hydrogen,

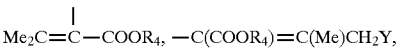

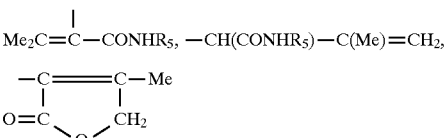

wherein
$R_4$ is hydrogen, methyl, benzyl or some other protective group,
$R_5$ is hydrogen, alkyl, alkylaryl, a heterocyclic ring,
Y is a halo atom, and
$R_6$ is halo, —$OR_7$ or —NH—$R_8$-,
wherein R₇ is hydrogen, alkyl or alkylaryl, or an alkali metal or DBN group, and R₈ is hydrogen, alkyl, alkylaryl or a substituted heterocyclic ring, by the reaction with tetrabutyl ammonium halide e.g. bromide, with halogen such as bromine or bromine on a polymer carrier [J. Johar, M. Zupan and B. Šket, J. Chem. Soc. Perkin Trans. I, 2059, (1982)] or with a halogenating agent wherein halogen has a positive charge e.g. N-chlorosuccinimide or N-bromosuccinimide in an organic solvent e.g. chloroform, tetrahydrofuran, methylene chloride or a mixture of methylene chloride and dioxan, by stirring the reaction solution at room temperature for 1 to 12 hours and after the treatment 2-halo derivatives of the general formula I, wherein X is halo and the radicals have the above meanings, are isolated. The obtained 2-halo derivatives of the general formula I, wherein X is halo, are subjected to a reaction with silver tetrafluoroborate and alcohols e.g. methanol to obtain derivatives of the general formula I wherein X is an alkoxy group e.g. methoxy group and R₁ is hydrogen or bromo, R₂ is hydrogen or bromo.

R₃ is hydrogen,

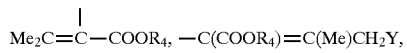

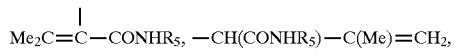

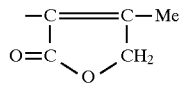

wherein

R₄ is hydrogen, methyl, benzyl or some other protective group,

R₅ is hydrogen, alkyl, alkylaryl, a heterocyclic ring,

Y is a halo atom, or 2-halo derivatives of the general formula I, wherein X is halo and the radicals have the above meanings, are subjected to a reaction with silver nitrate in 2-propanol to obtain derivatives of the general formula I, wherein X is nitroxy group and R₁ is hydrogen or bromo, R₂ is hydrogen or bromo, R₃ is hydrogen,

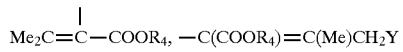

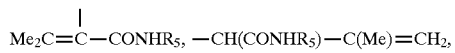

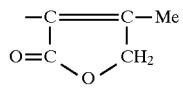

wherein

R₄ is hydrogen, methyl, benzyl or some other protective group,

R₅ is hydrogen, alkyl, alkylaryl, a heterocyclic ring,

Y is a halo atom, or derivatives of the general formula I wherein

R₁ is hydrogen or bromo,

R₂ is hydrogen or bromo,

R₃ is Me₂C=C—COOR₄, —C(COOR₄)=C(Me)CH₂Y, wherein

R₄ is benzyl or some other protective group,

Y is a halo atom, and

X is a halo atom, an alkoxy group, nitroxy group, are subjected to the reaction of the removal of the protective group e.g. benzyl, with aluminum trichloride, to obtain a product I, wherein R₁ is hydrogen or bromo, R₂ is hydrogen or bromo, R₃ is Me₂C=C—COOR₄, —C(COOR)=C(Me)CH₂Y, wherein R₄ is hydrogen, Y is a halo atom, and X is a halo atom, an alkoxy group, nitroxy group.

6,6-dibromopenicillanic acid derivatives are prepared from 6-aminopenicillanic acid according to well-known processes (R. A. Volkmann, R. D. Carroll, R. B. Drolet, M. L. Elliott, B. S. Moore. J. Org. Chem. 47, (1982) 3344–5; and Wayne E. Barth, U.S. Pat. No. 4,234,579).

The starting sulfinic acid derivatives are prepared according to DE appln. P 42 300 53.3 of 8 Sep. 1992; PCT/EP appln. 93/0242800 of 8 Sep. 1993.

The object of the present invention is a series of newly synthesised substances, which are prepared starting from sulfinic acid derivatives of azetidinones, preferably 2-sulfinamides of azetidinones with various substituents on azetidinone nitrogen. The object of the present invention is also a novel process that is simple and readily feasible and by means of which the novel substances are obtained in high yields.

Still another object of the invention is the use of the said substances as useful intermediates in the preparation of different beta lactam analogues such as 1-oxapenems (Masyuki Murakami, Tsutomu Auki, Munenuri Matasura and Wataru Nagata, J. Antibiot. 43 (1990) 1441–49; H. R. Pfaendler, T. Neumann and R. Bartsch, Synthesis (1992) 1179) or penems (V. M. Girijavallabhan, A. K. Ganguly, S. W. McCombie, P. Pinto, R. Rizvi, Tetrahedron Lett. 22, (1981) 3485–88; C. M. D. Beels, M. S. Abu Rabie, J. Chem. Soc. Chem. Commun. 1979, 665) or 1-oxacephalosporins (U.S. Pat. No. 4,013,653, U.S. Pat. No. 4,234,724, U.S. Pat. No. 4,159,984) or the present invention offers great possibilities for transformations into other beta lactam analogues, monobactams or cyclic compounds.

A further object of the present invention is the use of these compounds as components in pharmaceutical compositions having antibacterial, synergistic, antitumour or antagonistic action. The compounds of this invention may be used in the same manner as are the prior art azetidines, the particulars of which can be determined without undue experimentation. For instance, see U.S. patent application Ser. No. 08/272, 206, disclosure of which is incorporated herein by reference. The invention is illustrated by the following non-limiting Examples.

EXAMPLE 1

3,3-dibromo-2-methoxy-alpha-(1-methylethylidene)-4-oxo-1-azetidine acetic acid benzyl ester a) 3,3-dibromo-alpha-(1-methylethylidene)-2-[(5-methyl-isoxazole-3-yl)-aminosulfinyl]-4-oxo-1-azetidine acetic acid benzyl ester (5.61 g; 0.01 mole) was dissolved in chloroform (120 mL), bromine on a polymer carrier (12.5 g; the content of bromide bound to the polymer matrix with polyvinylpyrrolidone was 26%, 0.02 mole) (prepared according to J. Johar, M. Zupan and B. Šket, J. Chem. Soc. Perkin Trans. I, 2059, (1982)) was added and it was stirred for 12 hours at room temperature. The polymer was sucked off and the filtrate was evaporated to dryness. The obtained product was passed through a Merck 60 silica gel column with methylene chloride and thereafter 2,3,3-tribromo-alpha-(1-methylethylidene)-4-oxo-1-azetidine acetic acid benzyl ester (2.36 g, 47.6%) was isolated, m.p. 68°–70° C.

Rf 0.72 (methylene chloride).

IR (KBr) ν: 1795 (vs), 1730 (s), 1635 (m), 1395 (m), 1375 (m), 1270 (m), 1225 (vs) 1125–1070 (m), 815 (m), 700 (m) cm$^{-1}$.

$^1$H NMR (CDCl$_3$) δ: 2.00 (3H, s, Me), 2.34 (3H, s, Me), 5.16 and 5.25 (each 1H d, J=12 Hz, CH$_2$Ph), 6.30 (1H, s, C$_2$—H), 7.36 (5H, s, Ar) ppm.

$^{13}$C (CDCl$_3$) APT: 22.35 and 23.87 (2 Me), 55.67 (C$_3$—Br$_2$), 67.44 (CH$_2$Ph), 74.08 (C$_2$H), 117.03 (N—C=), 128.78 (Ph), 135.11 (C—Ph), 158.07 (COO), 159.95 (=C (Me)$_2$), 162.28 (C=O).

Anal. C$_{15}$H$_{14}$Br$_3$NO$_3$: calc.: C 36.32; H 2.84; N 2.82% found: C 36.61; H 2.15; N, 2.76% Mol. weight: 496.018; m/e 477 (—H$_2$O), 416 (—Br), 398 (—H$_2$O), 404 (—CH$_2$Ph).

To a solution of 2,3,3-tribromo-alpha-(1-methylethylidene)-4-oxo-1-azetidine acetic acid benzyl ester (0.50 g; 1 mmole) in methanol (50 ml), silver tetrafluoroborate (0.78 g; 4 mmole) was added and it was stirred at room temperature for 1 hour. The reaction mixture was filtered and the filtrate was evaporated to an oily residue (0.40 g, 89.5%).

Rf 0.54 (methylene chloride).

IR (film) ν: 3520 (s), 1760–1700 (vs). 1630 (s), 1395 (s), 1370 (s), 1210 (vs), 1150–1030 (vs) 765 (m) cm$^{-1}$.

$^1$H NMR (CDCl$_3$, 300 MHz) δ: 1.99 (3H, s, Me), 2.30 (3H, s, Me), 3.46 (3H, s, OCH$_3$) 5.12 (1H, s, C$_2$—H), 5.14 and 5.28 (2H, 2d, J=11 Hz, CH$_2$Ph), 7.38 (5H, m, Ar) ppm.

b) 3,3-dibromo-alpha-(1-methylethylidene)-2-[(5-methyl-isoxazole-3-yl)-aminosulfinyl]-4-oxo-1-azetidine acetic acid benzyl ester (5.61 g; 0.01 mole) was dissolved in chloroform (120 mL), N-bromosuccinimide (7.12 g; 0.04 mole) was added to the reaction mixture and it was stirred for two hours at room temperature. The reaction mixture was evaporated, methylene chloride and n-hexane were added to the dry residue, the precipitate was sucked off and the filtrate was evaporated to a dry residue. The obtained product was purified by flash chromatography with the solvent system petroleum ether-methylene chloride (1:1). There was obtained 2,3,3-tribromo-alpha-(1-methylethylidene)-4-oxo-1-azetidine acetic acid benzyl ester (3.05 g, 61.5%), which was subjected to a reaction with silver tetrafluoroborate in methanol analogously to the reaction described under 1a. After isolation 3,3-dibromo-2-methoxy-alpha-(1-methylethylidene)-4-oxo-1-azetidine acetic acid benzyl ester with spectroscopic data identical to those disclosed under 1a was obtained.

c) 3,3-dibromo-alpha-(1-methylethylidene)-2-[(5-methyl-isoxazole-3-yl)-aminosulfinyl]-4-oxo-1-azetidine acetic acid benzyl ester (5.61 g; 0.01 mole) was dissolved in chloroform (120 mL), bromine (4.1 mL, 12.78 g, 0.08 mole) was added to the reaction mixture and it was stirred at room temperature for 45 minutes. The reaction mixture was evaporated to dryness, treated with isopropanol (30 mL) at −5° C., the precipitate (1.287 g) was sucked off and the filtrate was evaporated to dryness (4.180 g). The dried filtrate was passed through a Merck 60 silica gel column with methylene chloride as the eluent to obtain another 2.20 g of the product. In the total 3.48 g (70.5%) of 2,3,3-tribromo-alpha-(1-methylethylidene)-4-oxo-1-azetidine acetic acid benzyl ester were obtained, which was subjected to a reaction with silver tetrafluoroborate in methanol analogously to the reaction described under 1a. After isolation 3,3-dibromo-2-methoxy-alpha-(1-methylethylidene)-4-oxo-1-azetidine acetic acid benzyl ester with spectroscopic data identical to those disclosed under 1a was obtained.

d) 3,3-dibromo-alpha-(1-methylethylidene)-2-[benzylaminosulfinyl]-4-oxo-1-azetidine acetic acid benzyl ester (5.7 g; 0.01 mole) was dissolved in chloroform (120 mL), bromine on a polymer carrier (18.75 g; the content of bromine bound to the polymer matrix with polyvinylpyrrolidone was 26%, 0.03 mole) was added and it was stirred at room temperature for 48 hours. Then the polymer was sucked off and the filtrate was evaporated to dryness. The evaporated residue was passed through a silica gel column with methylene chloride to isolate 2,3,3-tribromo-alpha-(1-methylethylidene)-4-oxo-1-azetidine acetic acid benzyl ester (2.73 g; 55.0%), which was subjected to a reaction with silver tetrafluoroborate in methanol analogously to the reaction described under 1a. After isolation 3,3-dibromo-2-methoxy-alpha-(1-methylethylidene)-4-oxo-1-azetidine acetic acid benzyl ester with spectroscopic data identical to those disclosed under 1a was obtained.

e) 3,3-dibromo-alpha-(1-methylethylidene)-2-[(5-methyl-isoxazole-3-yl)-aminosulfinyl]-4-oxo-1-azetidine acetic acid benzyl ester (5.61 g; 0.01 mole) was suspended in chloroform (110 mL), N-chlorosuccinimide (5.34 g; 0.04 mole) was added and it was stirred at room temperature for 8 hours. The reaction mixture was evaporated, methylene chloride and n-hexane were added to the dry residue, the precipitate was sucked off and the filtrate was evaporated to a dry residue (4.88 g). The obtained product was purified by flash chromatography with the solvent system petroleum ether-methylene chloride (1:1). After evaporating the solution and drying at 0.0133 mbar, there crystallized 3,3-dibromo-2-chloro-alpha-(1-methylethylidene)-4-oxo-1-azetidine acetic acid benzyl ester (3.41 g; 75.6%, m.p. 64°–66° C.

Rf 0.70 (methylene chloride).

IR (KBr) ν: 1795 (vs), 1730 (s), 1635 (m), 1395 (m), 1375 (m), 1270 (m), 1220 (s), 1125–1070 (b, m), 820 (m), 700 (m) cm$^{-1}$.

$^1$H NMR (CDCl$_3$), 300 MHz) δ: 2.00 and 2.35 (2s, 6H, 2Me), 5.16 and 5.25 (each 1H, d, J=12 Hz, CH$_2$Ph), 6.06 (s, 1H, C$_2$—H), 7.37 (s, 5H, Ar) ppm.

$^{13}$C (CDCl$_3$) APT: 22.28 and 23.81 (2 Me); 56.55 (C$_3$—Br$_2$); 67.43 (CH$_2$Ph); 81.30 (C$_2$—H), 116.75 (N—C=); 128.94 (Ph); 135.13 (C—Ph); 158.51 (COO); 160.27 (=C (Me)$_2$).

Mol. weight: 451.558; M/E 433 (—H$_2$O); 416 (—Cl); 360 (—CH$_2$Ph).

To a solution of 3,3-dibromo-2-chloro-alpha-(1-methylethylidene)-4-oxo-1-azetidine acetic acid benzyl ester (0.045 g; 0.1 mmole) in methanol (5 ml), silver tetrafluoroborate (0.078 g; 0.4 mmole) was added and the reaction mixture was heated at reflux for 15 hours. After the treatment of the reaction mixture as described under 1a, 3,3-dibromo-2-methoxy-alpha-(1-methylethylidene)-4-oxo-1-azetidine acetic acid benzyl ester with spectroscopic data identical to those disclosed under 1a was obtained.

f) 3,3-dibromo-alpha-(1-methylethylidene)-2-[benzylaminosulfinyl]-4-oxo-1-azetidine acetic acid benzyl ester (5.7 g; 0.01 mole) was subjected to the reactions as described under 1e and after isolation 3,3-dibromo-2-methoxy-alpha-(1-methylethylidene)-4-oxo-1-azetidine acetic acid benzyl ester with spectroscopic data identical to those disclosed under 1a was obtained.

EXAMPLE 2

3,3-dibromo-2-methoxy-alpha-(1-methylethylidene)-4-oxo-1-azetidine acetic acid a) To an ice-cooled suspension of aluminum trichloride (1.6 g; 0.012 mole) in methylene chloride (55 mL) in a nitrogen stream a solution of 3,3-dibromo-2-chloro-alpha-(1-methylethylidene)-4-oxo-1-azetidine acetic acid benzyl ester (1.5 g; 0.003 mole) and anisole (2.79 g; 2.7 mL, 0.024 mole) in methylene chloride (55 mL) was added and then it was stirred for half an hour at room temperature. Ethyl acetate (60 mL) and 0.1N hydrochloric acid (60 mL) were added to the reaction mixture and the layers were separated. The ethyl acetate layer was extracted with a 5% aqueous sodium hydrogen carbonate solution (2×50 mL) and the layers were separated. The aqueous layer was acidified with 0.1N hydrochloric acid to pH 1, then fresh ethyl acetate (60 mL) and sodium chloride were added and the layers were again separated. The ethyl acetate layer was washed with a saturated salt solution, dried and evaporated to a dry whitish powdery residue, 3,3-dibromo-2-chloro-alpha-(1-methylethylidene)-4-oxo-1-azetidine acetic acid (0.9 g; 75.0%), m.p. 106°–110° C.

Rf=0.50 (ethyl acetate-methanol (3:1))

IR (KBr) $\nu$: 1800 (vs), 1700 (s), 1630 (m), 1430 (m), 1370 (m), 1285 (m), 1245 (m) cm$^{-1}$.

$^1$H NMR (CDCl$_3$, 300 MHz) $\delta$: 2.06 (3H, s, Me), 2.39 (3H, s, Me) and 6.28 (1H, s, C2—H) and 9.57 (1H, b, COOH) ppm.

$^{13}$C (NMR) (CDCl$_3$, 300 MHz, APT) $\delta$: 22.51 and 24.11 (2 Me); 56.25 (C-3); 80.87 (C-2); 116.06 [(=C(COOH)], 158.21, 163.36 and 168.24 (=C(Me)$_2$, C=O and COOH) ppm.

To a solution of 3,3-dibromo-2-chloro-alpha-(1-methylethylidene)-4-oxo-1-azetidine acetic acid (0.361 g; 1 mmole) in methanol (50 mL) silver tetrafluoroborate (0.780 g; 4.0 mmole) was added and it was stirred at room temperature for 24 hours. The precipitate was sucked off and the filtrate was evaporated to a dry residue. To the residue after evaporation there were added methylene chloride and sodium hydrogen carbonate solutions, the layers were well shaken and separated, the aqueous layer was acidified to pH 1 with 0.1N hydrochloric acid and was again extracted with methylene chloride, dried (Na$_2$SO$_4$) and evaporated to an oily residue (0.080 g; 22%).

Rf 0.40 (ethyl acetate-methanol (3:1))

Rf 0.65 (n-butanol-ethanol-water (7:1:2))

IR(film) $\nu$: 1795 (vs), 1700 (s), 1375 (m), 1265 (vs), 910 (m), 735 (vs) cm$^{-1}$.

$^1$H NMR (CDCl$_3$, 300 MHz) $\delta$: 2.05 and 2.34 (6H, 2s, 2 Me), 3.61 (3H, s, OCH$_3$), 5.35 (1H, s, C$_2$—H) ppm.

b) To an ice-cooled suspension of aluminum trichloride (0.400 g; 0.003 mole) in methylene chloride (15 mL) in a nitrogen stream a solution of 2,3,3-tribromo-alpha-(1-methylethylidene)-4-oxo-1-azetidine acetic acid benzyl ester (0.496 g; 0.001 mole) and anisole (0.648 g; 0.65 mL, 0.006 mole) in methylene chloride (15 mL) was added and then it was stirred for half an hour at room temperature. Ethyl acetate (15 mL) and 0.1N hydrochloric acid (5 mL) were added to the reaction mixture and the layers were separated. The ethyl acetate layer was extracted with a 5% sodium hydrogen carbonate solution (2×20 mL) and the layers were separated. The aqueous layer was acidified with 0.1N hydrochloric acid to pH 1, then fresh ethyl acetate (20 mL) and sodium chloride were added and the layers were again separated. The ethyl acetate layer was washed with a saturated salt solution, dried and evaporated to a dry residue and again dried at 0.133 mbar, whereat 2,3,3-tribromo-alpha-(1-methyl- ethylidene)-4-oxo-1-azetidine acetic acid (0.219 g, 54.0%), m.p. 124°–6° C. crystallized.

Rf=0.50 (ethyl acetate-methanol (3:1))

IR (KBr) $\nu$: 1800 (vs), 1700 (s), 1630 (m), 1430 (m), 1370 (m), 1285 (m), 1245 (m) cm$^{-1}$.

$^1$H NMR (DMSO-d$_6$, 90 MHz) $\delta$: 1.89 (3H, s, Me), 2.25 (3H, s, Me) and 6.73 (1H, s, C2—H) ppm.

$^{13}$C NMR(DMSO-d$_6$, 300 MHz) $\delta$: 2.17 (Me); 23.00 (Me), 35.32 (C$_3$—Br$_2$), 74.37 (C2—H), 118.04 (=C (COOH), 156.10, 158.01, 164.00 (=C(Me)$_2$, C=O and COOH) ppm.

To a solution of 2,3,3-tribromo-alpha-(1-methylethylidene)-4-oxo-1-azetidine acetic acid (0.45 g; 1 mmole) in methanol (20 mL) silver tetrafluoroborate (0.780 g; 4.0 mmole) was added and it was stirred at room temperature for 24 hours. After isolation as described under 2a, 3,3-dibromo-2-methoxy-alpha-(1-methylethylidene)-4-oxo-1-azetidine acetic acid with spectroscopic data identical to those disclosed under 2a was obtained.

c) To an ice-cooled suspension of aluminum trichloride (0.400 g; 0.003 mole) in methylene chloride (15 mL) in a nitrogen stream a solution of 2-methoxy-3,3-dibromo-alpha-(1-methylethylidene)-4-oxo-1-azetidine acetic acid benzyl ester (0.447 g; 0.001 mole) and anisole (0.648 g; 0.65 mL, 0.006 mole) in methylene chloride (15 mL) was added and then it was stirred for half an hour at room temperature. Ethyl acetate (15 mL) and 0.1N hydrochloric acid (5 mL) were added to the reaction mixture and the layers were separated. The ethyl acetate layer was extracted with a 5% sodium hydrogen carbonate solution (2×20 mL) and the layers were separated. The aqueous layer was acidified with 0.1N hydrochloric acid to pH 1, then fresh ethyl acetate (20 mL) and sodium chloride were added and the layers were again separated. The ethyl acetate layer was washed with a saturated salt solution, dried and evaporated to a dry residue to obtain 3,3-dibromo-2-methoxy-alpha-(1-methylethylidene)-4-oxo-1-azetidine acetic acid, which was identical to the one disclosed under 2a.

EXAMPLE 3

2,3,3-tribromo-alpha-(1-bromomethylethylidene)-4-oxo-1-azetidine acetic acid benzyl ester 3,3-dibromo-alpha-(1-methylethenyl)-2-[(5-methyl-isoxazole-3-yl)-aminosulfinyl]-4-oxo-1-azetidine acetic acid benzyl ester (5.61 g: 0.01 mole) was suspended in chloroform (210 mL), bromine (4.1 mL, 12.78 g, 0.08 mole) was added and it was stirred at room temperature for 2 hours. Then the reaction mixture was evaporated to dryness (6.4 g) and passed through a silica gel column with the methylene chloride-petroleum ether (6:4) mixture. An isomeric mixture (4.46 g; 77.6%) was obtained. By further purification by chromatography on a silica gel column a less polar isomer with m.p. 84°–5° C. was isolated.

Rf 0.60 (methylene chloride-petroleum ether (6:4))

IR (film) $\nu$: 1790 (vs), 1720 (vs), 1640 (m), 1390 (m), 1370 (s), 1240 (s), 1100 (s) 810 (s) cm$^{-1}$.

$^1$H NMR (CDCl$_3$, 300 MHz) $\delta$: 2.12 (3H, s, Me), 4.39 and 4.71 (each 1H d, J=9.4 Hz, CH$_2$Br), 5.20 and 5.31 (each 1H, d, J=12 Hz, CH$_2$Ph), 6.31 (s, 1H, C$_2$—H) and 7.38 (5H, s, Ar) ppm.

$^{13}$C (CDCl$_3$, 300 MHz) APT $\delta$: 20.40 (Me), 29.72 (CH$_2$Br), 55.29 (CBr$_2$), 67.98 (CH$_2$Ph), 73.15 (C2—H) and 119.10; 128.80; 134.29, 154.71; 157.160, 161.09.

MH$^+$ 576, M$^+$(Br$_4$) 575

Anal. C$_{15}$H$_{13}$Br$_4$NO$_3$; calc.: C 31.33; H 2.28;N 2.44% found: C 31.63; H 2.09; N 2.27%

By further passing of the solvent mixture methylene chloride-petroleum ether (6:4) a more polar isomer (oil) was isolated.

Rf 0.50 (methylene chloride-petroleum ether (6:4))

IR (film) ν: 1800 (vs), 1725 (vs), 1625 (m), 1450 (m), 1390–60 (s), 1210 (vs), 1105 (s) 810 (s) cm$^{-1}$.

$^1$H NMR (CDCl$_3$, 300 MHz) δ: 2.42 (3H, s, Me), 4.00 (s, 2H, CH$_2$Br), 5.18 and 5.27 (each 1H d, J=12 Hz, CH$_2$Ph), 6.30 (s, 1H, C$_2$—H) and 7.36 (5H, s, Ar) ppm.

$^{13}$C APT (CDCl3, 300 MHz)) APT δ: 19.39 (Me), 31.38 (CH$_2$Ph), 55.22 (CBr$_2$), 67.87 (CH$_2$Br), 72.97 (C2—H) and 118.23 (C$_2$); 128.78 (Ph); 134.37; 154.59; 158.29; and 161.21 ppm.

EXAMPLE 4

3,3,4-tribromo-1-(4-methyl-2-oxo-2,5-dihydro-furan-3-yl)-azetidine-2-one

To an ice-cooled suspension (−5° C.) of aluminum trichloride (1.064 g; 0.008 mole) in methylene chloride (30 mL) in a nitrogen stream a solution of 2,3,3-tribromo-alpha-(1-bromomethylidene)-4-oxo-1-azetidine acetic acid benzyl ester (0.575 g, 0.001 mole) and anisole (2.59 g; 2.6 mL, 0.024 mole) was added drop by drop for an hour and then it was stirred at room temperature for another hour. To the reaction mixture ethyl acetate (15 mL), 0.1N hydrochloric acid to pH 1 and sodium chloride were added. The layers were separated. The aqueous layer was extracted again with ethyl acetate, the combined ethyl acetate phases were dried and evaporated to a dry residue. The dry residue was purified by chromatography on a silica gel column, at first with the solvent system methylene chloride-methanol (9:1). 0.33 g (73%) of the product was obtained, which was further purified by chromatography on a silica gel column with methylene chloride. A product with m.p. 164°–66° C. (dec.) was obtained.

Rf 0.55 (methylene chloride)

Rf 0.25 (methylene chloride-petroleum ether (6:4))

IR (KBr) ν: 1785 (vs), 1700 (s), 1630 (m), 1425 (m), 1370 (s), 1115 (s), 815 (m) cm$^{-1}$.

$^1$H NMR (300 MHz, CDCl$_3$)) δ: 2.26 (s, 3H, Me), 4.77 and 4.84 (2d, 2H, J=17.8 Hz, —CH$_2$) and 6.92 (1H, s, C$_2$—H) ppm.

$^{13}$C NMR APT (300 MHz, CDCl$_3$) δ: 13.02 (Me), 55.53 (CBr$_2$), 69.789 (C$_2$—H), 72.01 (—CH$_2$), 118.31 (C$_2$, 153.99, 156.49 and 167.67 (C$_3$, C$_4$' and C$_1$).

EXAMPLE 5

3,3-dibromo-2-chloro-alpha-(1-methylethylidene)-4-oxo-1-azetidine acetic acid benzylamide 3,3-dibromo-2-chloro-alpha-(1-methylethylidene)-4-oxo-1-azetidine acetic acid (0.180 g, 5 mmole) was dissolved in methylene chloride (10 mL), cooled to −10° C., thionyl chloride (2 mL) was added and it was stirred for one hour at −10° C. and then again for one hour at room temperature. Then the reaction mixture was evaporated, to the dry residue benzene (2×10 mL) was added and evaporated after each addition. Benzylamine (0.22 mL; 0.21 g; 20 mmole) was added to the residue dissolved in methylene chloride (10 mL) and it was stirred at a room temperature for 2 hours. The precipitate was sucked off and the filtrate was evaporated to a dry residue (0.205 g). The obtained product was purified by flash chromatography with methylene chloride as the eluent and then an oily product was isolated, which by drying at 0.0133 mbar was transformed into a foam (0.09 g; 44.0%).

Rf 0.33 (methylene chloride)

IR (film) ν max: 3300 (s), 1800 (vs), 1660 (vs), 1640 (vs), 1520 (vs), 1365 (vs), 1130 (s), 1100 (s), 812 (s), 700 (s) cm$^{-1}$.

$^1$H NMR (CDCl$_3$, 300 MHz) δ: 1.86 and 2.07 (6H, 2s, 2 Me), 4.49 (2H, m, N—CH$_2$), 6.07 (1H, s, C$_2$—H), 6.19 (1H, s, NH—C) and 7.29–7.36 (5H, m, Ar) ppm.

$^1$H NMR (CDCl$_3$+D$_2$O, 300 MHz) δ : 1.86 and 2.07 (6H, 2s, 2Me), 4.49 (2H, ABq, N—CH$_2$), 6.07 (1H, s, C$_2$H) and 7.28–7.37 (5H, m, Ar) ppm.

EXAMPLE 6

3,3-dibromo-2-chloro-alpha-(1-methylethenyl)-4-oxo-1-azetidine acetic acid benzylamide To a solution of 6,6-dibromopenicillanic acid benzylamide sulfoxide (0.70 g, 1.5 mmole) in dry toluene (75 mL) N-chlorosuccinimide (0.40 gl 3 mmole) was added and it was heated at reflux for 3 hours. The reaction mixture was evaporated to a dry residue, then ether was added, the precipitate was sucked off and the filtrate was evaporated to dryness (0.68 g). The obtained product was purified by chromatography on a silica gel column with methylene chloride as the eluent. An oily sirupy product (0.20 g, 29.9%) was obtained.

Rf 0.28 (methylene chloride)

IR (film) ν max: 3300 (m), 1795 (vs), 1705 (vs), 1525 (m), 1345 (m), 1180 (s), 7000 (m) cm$^{-1}$.

$^1$H NMR (CDCl$_3$, 300 MHz) δ: 1.81 (3H, s, Me), 4.42 and 4.32 (each 1H, dd J=5.5, 6.0 and 15 Hz, NH—CH$_2$), 4.73 (1H, s, CH—CON), 5.16 and 5.21 (2H, 2s, =CH$_2$), 6.36 (1H, s, C$_2$—H), 6.50 (1H, m, NH) and 7.27–7.36 (5H, m, Ar) ppm.

$^1$H NMR (D$_2$O) (300 MHz) δ: 1.85 (3H, s, Me), 4.39 and 4.50 (2H, for each 1H d, J=15 Hz, N—CH$_2$Ph), 4.73 (1H, s, CH—CON), 5.16 and 5.21 (2H, 2s, =CH$_2$), 6.35 (1H, s, C$_2$—H), 7.28–7.36 (5H, m, Ar) ppm.

EXAMPLE 7

3,3-dibromo-alpha-(1-methylethylidene)-2-nitroxy-4-oxo-1-azetidine acetic acid benzyl ester a) 2,3,3-tribromo-alpha-(1-methylethylidene)-4-oxo-1-azetidine acetic acid benzyl ester (0.744 g; 0.0015 mole) was dissolved in 2-propanol (20 mL), silver nitrate (1.01 g; 0.0060 mole) was added and it was heated in a nitrogen stream at the boiling temperature for one hour. Then the reaction mixture was filtered and the filtrate was evaporated to dryness. Methylene chloride was added to the residue after evaporation, the precipitate was sucked off and the filtrate was evaporated to dryness (0.466 g; 65%). The obtained product was passed through a silica gel column with methylene chloride and then a substance was isolated, which crystallized upon standing (0.42 g; 58.13%). M.p. 69°–71° C.

Rf=0.75 (methylene chloride)

IR (KBr) ν: 1805 (vs), 1730 (vs), 1660 (vs), 1390 (m), 1375 (m), 1285 (vs), 1225 (vs), 1140 (s), 1080 (m), 830 (s), 760 (m), 700 (m) cm$^{-1}$.

$^1$H NMR (CDCl$_3$ (300 MHz) δ: 1.99 (3H, s, Me), 2.32 (3H, s, Me), 5.16 and 5.27 (each 1H d, J=12 Hz, CH$_2$Ph), 6.42 (1H, s, C$_2$H), 7.37 (5H, s, Ar) ppm.

$^{13}$C (CDCl$_3$ APT: 21.97 and 23.70 (2 Me), 52.93 (C$_3$—Br$_2$), 67.34 (CH$_2$Ph), 90.89 (C$_2$—H), 116.65 (N—C=), 128.61 (Ph), 134.66 (C—Ph), 158.29 (COO), 159.63 (=C (Me)$_2$), 161.67 (C=O).

Mol. weight: 478.11; m/e 432 (—NO$_2$), 398 (—Br), 352 (—NO$_2$).

b) 3,3-dibromo-alpha-(1-methylethylidene)-2-nitroxy-4-oxo-1-azetidine acetic acid benzyl ester may be obtained analogously as under 7a, only the starting substance is 3,3-dibromo-2-chloro-alpha-(1-methylethylidene)-4-oxo-1-azetidine acetic acid benzyl ester (0.676 g, 0.0015 mole).

EXAMPLE 8
3-bromo-2-chloro-alpha-(1-methylethylidene)-4-oxo-1-azetidine acetic acid methyl ester 3-bromo-alpha-(1-methylethylidene)-2-[(5-methyl-isoxazole-3-yl)-aminosulfinyl]-4-oxo-1-azetidine acetic acid methyl ester (4.06 g; 0.01 mole) was suspended in chloroform (110 mL), N-chlorosuccinimide (5.34 g; 0.04 mole) was added and it was stirred for 8 hours at room temperature. The reaction mixture was treated as under 1e and purified by chromatography on a silica gel column by eluting with methylene chloride and thereafter two isomeric products were isolated: first a "trans" isomer (oil) was isolated, Rf 0.50 (methylene chloride)
IR (film) ν max: 1800 (vs), 1730 (vs), 1640 (m), 1435 (m), 1380 (vs), 1370 (vs), 1270 (s), 1225 (vs), 1125–1070 (bm), 810 (s) cm$^{-1}$.
$^1$H NMR (CDCl$_3$) (90 MHz) δ: 2.03 (3H, s, Me), 2.32 (3H, s, Me), 3.30 (3H, s, OCH$_3$), 5.05 and 5.95 (each 1H d, J=0.9 Hz, C$_2$—H and C$_3$—H) ppm.

and then a "cis" isomer (oil) was isolated,
Rf 0.40 (methylene chloride)
IR (film) ν max: 1800 (vs), 1730 (vs), 1643 (m), 1435 (m), 1375 (vs), 1670 (vs), 1270 (s), 1225 (vs), 1125–1070 (bm), 810 (s) cm$^1$.
$^1$H NMR (CDCl$_3$) (300 MHz) δ: 2.04 (3H, s, Me), 2.31 (3H, s, Me), 3.79 (3H, s, OCH$_3$), 5.33 and 6.10 (each 1H d, J=4 Hz, C$_2$—H and C$_3$—H) ppm.
Mol. weight: 294.960534

EXAMPLE 9
3-bromo-2-chloro-alpha-(1-methylethylidene)-4-oxo-1-azetidine acetic acid benzyl ester 3-bromo-alpha-(1-methylethylidene)-2-[(5-methyl-isoxazole-3-yl)-aminosulfinyl]4-oxo-1-azetidine acetic acid benzyl ester (4.82 g; 0.01 mole) was suspended in chloroform (110 mL), N-chlorosuccinimide (5.34 g; 0.04 mole) was added and it was stirred at room temperature for 8 hours. The reaction mixture was treated as under 1e and purified on a silica gel column by eluting with methylene chloride and thereafter two isomeric products were isolated: first a "trans" isomer (oil) was eluted, Rf 0.66 (methylene chloride)
IR (film) ν max: 1795 (vs), 1730 (s), 1635 (m), 1390 (m), 1375 (m), 1265 (m), 1220 (s), 1120–1070 (bm), 815 (m) and 700 (m) cm$^{-1}$.
$^1$H NMR (CDCl$_3$) (300 MHz) δ: 2.03 and 2.34 (6H, 2 s, 2 Me), 4.86 and 5.76 (each 1H d, J=0.9 Hz, C$_2$—H and C$_3$—H) and 7.37 (5H, s, Ar) ppm.

and then a "cis" isomer (oil) was isolated,
Rf 0.53 (methylene chloride)
IR (film) ν max: 1795 (vs), 1730 (s) 1635 (m), 1390 (m), 1375 (m), 1265 (m), 1220 (s), 1120–1070 (bm), 815 (m) and 700 (m) cm$^1$.
$^1$H NMR (CDCl$_3$) (300 MHz) δ: 2.04 (3)H, s, Me), 2.31 (3H, s, Me), 5.14 and 5.26 (each 1H, d, J=12 Hz, CH$_2$Ph), 5.19 and 5.9 (each 1H d, J=4 Hz, C$_2$—H and C$_3$—H), 7.31–7.42 (5H, m, Ar) ppm.
Mol. weight: 370.991834

EXAMPLE 10
3,3-dibromo-2-isopropoxy-alpha-(1-methylethylidene)-4-oxo-1-azetidine acetic acid benzyl ester To a solution of 2,3,3-tribromo-1-(1-methylethylidene)-4-oxo-1-azetidine acetic acid benzyl ester (0.248 g; 0.5 mmole) in 2-propanol (p.a., 10 mL) silver tetrafluoroborate (0.388 g; 2.0 mmole) was added and it was stirred at room temperature. After 10 minutes the suspension converted into a solution and the reaction was completed in one hour. The solution was filtered and the filtrate was evaporated to a dry residue. To the residue after evaporation methylene chloride was added, the precipitate was filtered, evaporated and again methylene chloride was added, the precipitate was filtered and the filtrate was evaporated to a dry residue. The residue after evaporation was purified by chromatography on a silica gel column with the solvent system ethyl acetate-methanol (95:5). The yield after drying in high vacuum was 0.130 g (54%).

Rf 0.55 (methylene chloride)
IR (100%): 3350 (w), 2980 (w), 1800 (vs), 1790 (vs), 1730 (vs), 1655 (m), 1500 (m), 1455 (m), 1390 (vs), 1370 (vs), 1335 (m), 1295 (s), 1265 (s), 1220 (vs), 1165 (vs), 1100 (vs), 1020 (s), 700 (vs) cm$^{-1}$.
$^1$H NMR (300 MHz, CDCl$_3$) δ: 1.085 and 1.216 (2d, 6H, J=6.2 MHz, Me$_2$—CH), 1.982 and 2.298 (2s, 6H, 2Me), 3.700–3.741 (m, 1H, J=6.2 Hz, CH), 5.117 and 5.292 (2H, 2d, J=12 Hz, CH$_2$Ph), 5.286 (s, 1H, C$_2$—H), 7.331–7.392 (m, 5H, Ar) ppm.

EXAMPLE 11
2,3,3-tribromo-alpha-(1-methylethylidene)-4-oxo-1-azetidine acetic acid benzylamide 2,3,3-tribromo-alpha-(1-methylethylidene)-4-oxo-1-azetidine acetic acid (0.406 g, 0.001 mole) was dissolved in methylene chloride (washed with water, dry, 20 mL), cooled to −10° C., thionyl chloride (4 mL) was added and it was stirred for one hour and then for another hour at room temperature. Then the reaction mixture was evaporated and to the dry residue benzene (2×20 mL) was added and evaporated after each addition. To the residue dissolved in methylene chloride (20 mL), benzylamine (0.30 mL, 0.00027 mole) dissolved in 10 ml methylene chloride to pH 7.0 was added and it was stirred at room temperature for one hour. The precipitate was sucked off and the filtrate was evaporated to a dry residue (0.241 g). The obtained product was purified by flash chromatography with methylene chloride as the eluent and thereafter an oily product was isolated, which upon drying at 0.0133 mbar was transformed into a foam (0.209 g). The part of the product remaining on the silica gel layer was eluted with methanol, evaporated to dryness and again purified by chromatography on a column with methylene chloride-acetone (10:0.3). Another 0.074 g of the product were obtained. In the total there were obtained 0.283 g (57.2%).

Rf 0.50 (methylene chloride-acetone (10:0.3))
IR (film): 3305 (m), 1800 (vs), 1670–1635 (vs), 1535–1510 (s), 1370 (vs), 1135 (s), 1100 (s), 810 (s), 705 (s) cm$^{-1}$.
$^1$H NMR (CDCl$_3$) (300 MHz) δ: 1.876 (s, 3H, Me), 2.085 (s, 3H, Me), 4.50–4.52 (m, 2H, NHCH$_2$Ph, z D$_2$O 4.506 2d, centre), 6.010 (bs, 1H, NH, diappears with D$_2$O), 6.301 (s, 1H, C2—H), 7.303–7.376 (m, 5H, Ar) ppm.
MS FAB+MW 492, MH+493, (3Br).

EXAMPLE 12
3,3-dibromo-2-methoxy-alpha-(1-methylethylidene)-4-oxo-1-azetidine acetic acid benzylamide To a solution of 2,3,3-tribromo-alpha-(1-methylethylidene)-4-oxo-1-azetidine acetic acid benzylamide (0.074 g; 0.15 mmole) in MeOH (5 mL, silver tetrafluoroborate (0.117 g; 0.60 mmole) was added and it was stirred at room temperature. After the completed reaction it was filtered, methylene chloride was added, it was filtered again and the filtrate was evaporated to dryness (0.136 g). The substance was purified by chromatography on a silica gel column with the solvent system methylene chloride-acetone (10:0.3); yield 0.033 g (50%) (white syrup).

Rf 0.4 methylene chloride-acetone (10:0.3)

IR (film): 3335 (m), 1800 (vs, 1675–1630 (s), 1520 (s), 1380 (vs), 1120 (s), 700 (vs) cm$^{-1}$.

$^1$H NMR (CDCl$_3$) (300 MHz) δ: 1.873 (s, 3H, Me), 2.156 (s, 3H, Me), 3.552 (s, 3H, OMe), 4.468–4.c95 (m, 2H, NHCH$_2$Ph, with D$_2$O 2d, 4.480 centre), 5.102 (s, 1H, C$_2$—H), 6.418 (b, 1H, NH, diappears with D$_2$O), 7.28–7.36 (m, 5H, Ar) ppm.

I claim:

1. 3-Bromo- and 3,3-dibromo-4-oxo-1-azetidines of the formula I

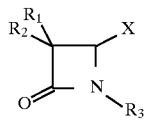

wherein
R$_1$ is hydrogen or bromo,
R$_2$ is hydrogen or bromo, wherein at least one of R$_1$ or R$_2$ is bromo,
R$_3$ is

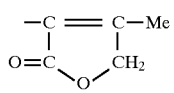

wherein
Me stands for methyl,
R$_4$ is hydrogen, methyl, benzyl or some other protective group,
R$_5$ is hydrogen, alkyl, or alkylaryl,
Y is a halo atom,
X is a halo atom, alkoxy group, or nitroxy group.

2. Compound according to claim 1, wherein R$_1$ is bromo, R$_2$ is bromo, R$_3$ is —C(COOR$_4$)=C(Me)CH$_2$Y, R$_4$ is benzyl, Y is bromo, X is bromo.

3. Compound according to claim 1, wherein R$_1$ is bromo, R$_2$ is bromo, R$_3$ is

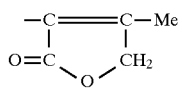

X is bromo.

4. Compound according to claim 1, wherein R$_1$ is bromo, R$_2$ is bromo, R$_3$ is

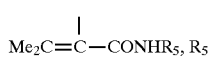

is benzyl, X is chloro.

5. Compound according to claim 1, wherein R$_1$ is bromo, R$_2$ is bromo, R$_3$ is —CH(CONHR$_5$)—C(Me)=CH$_2$, R$_5$ is benzyl, X is chloro.

6. Compound according to claim 1, wherein R$_1$ is bromo, R$_2$ is bromo, R$_3$ is

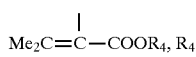

is benzyl, X is methoxy.

7. Compound according to claim 1, wherein R$_1$ is bromo, R$_2$ is bromo, R$_3$ is Me$_2$C=C—COOR$_4$, R$_4$ is hydrogen, X is methoxy.

8. 3,3-Dibromo-4-oxo-1-azetidines of the formula I

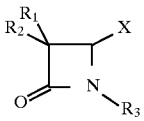

wherein
R$_1$ is bromo,
R$_2$ is bromo,
R$_3$ is

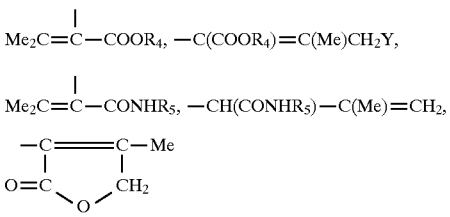

wherein
Me stands for methyl,
R$_4$ is hydrogen, methyl, or benzyl,
R$_5$ is hydrogen, alkyl, or alkylaryl,
Y is a halo atom,
X is a halo atom, alkoxy group, or nitroxy group.

9. A pharmaceutical composition effective in antibacterial therapy containing as active substance 4-oxo-azetidines of the formula I according to claim 8, a carrier and adjuvants.

10. Compound according to claim 1, wherein R$_1$ is bromo, R$_2$ is bromo, R$_3$ is

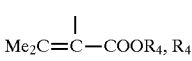

is benzyl, X is isopropoxy.

11. Compound according to claim 1, wherein R$_1$ is bromo, R$_2$ is bromo, R$_3$ is Me$_2$C=C—CONHR$_5$, R$_5$ is benzyl, X is bromo.

12. Compound according to claim 1, wherein R$_1$ is bromo, R$_2$ is bromo, R$_3$ is Me$_2$C=C—CONHR$_5$, R$_5$ is benzyl, X is methoxy.

13. A pharmaceutical composition effective in antibacterial therapy containing as active substance 3-bromo- or 3,3-Dibromo-4-oxo-1-azetidine of the formula I

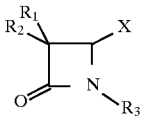

wherein
R$_1$ is hydrogen or bromo,
R$_2$ is hydrogen or bromo, wherein at least one of R$_1$ or R$_2$ is bromo,
R$_3$ is hydrogen,

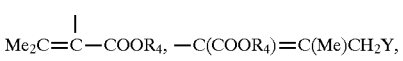

-continued

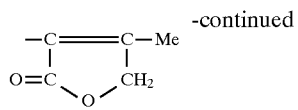

wherein

Me stands for methyl, $R_4$ is hydrogen, methyl, benzyl, or some other protective group, $R_5$ is hydrogen, alkyl, or alkylaryl, Y is a halo atom, X is a halo atom, alkoxy group, or nitroxy group; a carrier and adjuvants.

14. A pharmaceutical composition effective in antibacterial therapy containing as active substance a 4-oxo-azetidine of the formula I according to claim 1, a carrier and adjuvants.

* * * * *